(12) United States Patent
Yen et al.

(10) Patent No.: US 10,423,069 B2
(45) Date of Patent: Sep. 24, 2019

(54) WATER SOLUBLE PHOTOSENSITIVE RESIN COMPOSITION AND FILM USING SAME

(71) Applicant: Zhen Ding Technology Co., Ltd., Tayuan, Taoyuan (TW)

(72) Inventors: Chen-Feng Yen, Taoyuan (TW); Chang-Hung Lee, Taoyuan (TW); Yi-Fang Lin, Taoyuan (TW); Yen-Chin Hsiao, Taoyuan (TW); Shou-Jui Hsiang, Taoyuan (TW); Mao-Feng Hsu, Taoyuan (TW)

(73) Assignee: Zhen Ding Technology Co., Ltd., Tayuan, Taoyuan (TW)

(*) Notice: Subject to any disclaimer, the term of this patent is extended or adjusted under 35 U.S.C. 154(b) by 119 days.

(21) Appl. No.: 15/691,282

(22) Filed: Aug. 30, 2017

(65) Prior Publication Data
US 2018/0188649 A1 Jul. 5, 2018

(30) Foreign Application Priority Data
Dec. 30, 2016 (TW) ................. 105144074

(51) Int. Cl.
*G03F 7/029* (2006.01)
*H05K 1/03* (2006.01)
(Continued)

(52) U.S. Cl.
CPC ........... *G03F 7/029* (2013.01); *C07D 263/12* (2013.01); *C07D 263/14* (2013.01);
(Continued)

(58) Field of Classification Search
CPC . G03F 7/004; G03F 7/029; G03F 7/31; G03F 7/0388; G03F 7/07; H05K 1/0353;
(Continued)

(56) References Cited

U.S. PATENT DOCUMENTS

| | | | | |
|---|---|---|---|---|
| 6,258,510 B1* | 7/2001 | Maemoto | ................ | G03F 7/029 430/278.1 |
| 6,291,914 B1* | 9/2001 | Mukaiyama | ............. | B62D 6/10 310/68 B |

(Continued)

OTHER PUBLICATIONS

J.M Havard, Yoshida • • • etc, "Design of Photoresists with Reduced Environmental Impact. II. Water-Soluble Resists Based on Photocrosslinking of Poly(2-Isopropenyl-2-oxazoline)", Journal of Polymer Science: Part A: Polymer Chemistry, vol. 37, 1225-1236(1999).

*Primary Examiner* — Amanda C. Walke
(74) *Attorney, Agent, or Firm* — ScienBiziP, P.C.

(57) ABSTRACT

A non-toxic water soluble photosensitive resin composition able to function as a solder mask coating comprises a polymer containing oxazolinyl, a photosensitive monomer, and a photo-initiator. These elements are all water soluble or water dispersible. The polymer containing oxazolinyl and the photosensitive monomer have a plurality of carbon-carbon double bonds. The polymer containing oxazolinyl and the photosensitive monomer are polymerized to form a dense cross-linking network structure when the water soluble photosensitive resin composition is exposed to ultraviolet radiation. A film using the water soluble photosensitive resin composition is also provided.

20 Claims, 3 Drawing Sheets

(51) Int. Cl.
| | |
|---|---|
| *C09D 139/04* | (2006.01) |
| *C07D 263/12* | (2006.01) |
| *C07D 263/14* | (2006.01) |
| *C09D 133/06* | (2006.01) |
| *G03F 7/031* | (2006.01) |
| *G03F 7/038* | (2006.01) |
| *G03F 7/07* | (2006.01) |
| *H05K 3/28* | (2006.01) |
| *H05K 3/34* | (2006.01) |

(52) U.S. Cl.
CPC ....... *C09D 133/062* (2013.01); *C09D 139/04* (2013.01); *G03F 7/031* (2013.01); *G03F 7/0388* (2013.01); *G03F 7/07* (2013.01); *H05K 1/0353* (2013.01); *H05K 3/287* (2013.01); *H05K 3/3452* (2013.01)

(58) Field of Classification Search
CPC .. H05K 3/287; H05K 3/3452; C09D 133/062; C09D 139/04; C07D 263/12; C07D 263/14

USPC ...................................................... 430/270.1
See application file for complete search history.

(56) References Cited

U.S. PATENT DOCUMENTS

| | | | |
|---|---|---|---|
| 2001/0044482 A1* | 11/2001 | Hu ........................ | C08F 265/04 523/106 |
| 2007/0112106 A1* | 5/2007 | Otsuki ..................... | C09D 4/06 524/114 |
| 2008/0193880 A1* | 8/2008 | Nishibe ..................... | G03F 7/40 430/286.1 |
| 2009/0263744 A1 | 10/2009 | Kuroki | |
| 2015/0119497 A1* | 4/2015 | Matsui ................. | C09D 175/04 523/400 |
| 2017/0152333 A1* | 6/2017 | Zorn ...................... | C08F 212/08 |
| 2018/0039179 A1* | 2/2018 | Murai ..................... | G03F 7/095 |

* cited by examiner

WATER SOLUBLE PHOTOSENSITIVE RESIN COMPOSITION AND FILM USING SAME

FIELD

The subject matter herein generally relates to a resin composition, and more particularly, to a water soluble photosensitive resin composition, and a film using the water soluble photosensitive resin composition.

BACKGROUND

Printed circuit boards (PCBs) usually include solder mask coatings applied to the copper traces for protection against oxidation, and to prevent solder bridges being generated between adjacent solder pads. The solder mask coating is formed by a solder mask ink. Organic solvents, such as propylene glycol methyl ether acetate (PGMEA), methy ethyl ketone (MEK), ethylene glycol monobutyl ether (BCS), or toluene, are generally used in process of making the solder mask ink. The organic solvent is harmful to the environment. When using the solder mask ink to make PCB, an alkaline aqueous solution or an organic developer is used in developing process, which is also harmful to the environment.

BRIEF DESCRIPTION OF THE DRAWINGS

Implementations of the present technology will now be described, by way of example only, with reference to the attached figures.

DETAILED DESCRIPTION

Figure 1:
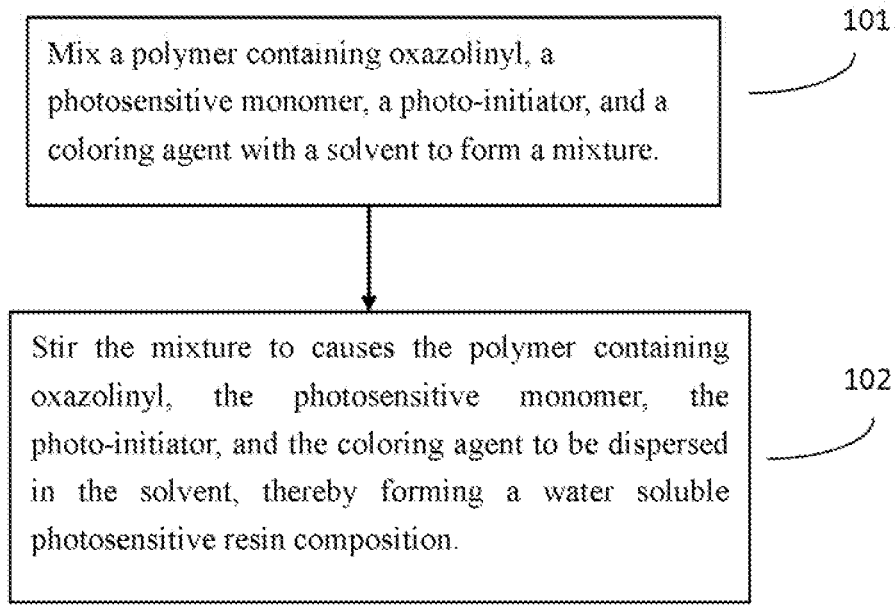
FIG. 1 is a flowchart of a method for making a water soluble photosensitive resin composition in accordance with an exemplary embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to illustrate details and features of the present disclosure better.

Several definitions that apply throughout this disclosure will now be presented.

The term "comprising" when utilized, means "including, but not necessarily limited to"; it specifically indicates open-ended inclusion or membership in the so-described combination, group, series, and the like. The term "about" when utilized, means "not only include the numerical value, but also include number closest to the numerical value".

An exemplary embodiment of a water soluble photosensitive resin composition comprises a polymer containing oxazolinyl, a photosensitive monomer, and a photo-initiator. Each of the polymer containing oxazolinyl, the photosensitive monomer, and the photo-initiator is water soluble or water dispersible.

Both of the polymer containing oxazolinyl and photosensitive monomer have a plurality of carbon-carbon double bonds (C=C), so that the polymer containing oxazolinyl and photosensitive monomer may be polymerized to form a dense cross-linking network structure when the water soluble photosensitive resin composition is exposed to ultraviolet radiation.

A chemical structure formula of the oxazolinyl is:

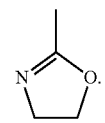

The polymer containing oxazolinyl is in an amount by weight of about 100 parts in the water soluble photosensitive resin composition, the photosensitive monomer is in an amount by weight of about 10 parts to about 50 parts in the water soluble photosensitive resin composition, and the photo-initiator is in an amount by weight of about 5 parts to about 15 parts in the water soluble photosensitive resin composition.

The polymer containing oxazolinyl has a molecular weight of about 6000 g/mol to about 100000 g/mol.

A chemical structure formula of the polymer containing oxazolinyl is:

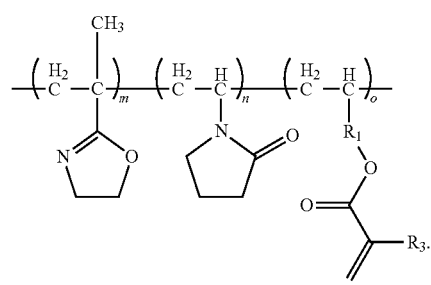

In the chemical structure formula of the polymer containing oxazolinyl above, the m, n, and o is each a positive integer. In at least one exemplary embodiment, the $R_1$ is $(CH_2)_k$, the k is a positive integer. The $R_3$ may be H or $CH_3$.

In the chemical structure formula of the polymer containing oxazolinyl above, the

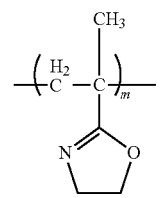

is heat curable, thereby the polymer containing oxazolinyl is heat curable. In other words, the polymer containing oxazolinyl can undergo a thermal solidifying reaction when heated. The

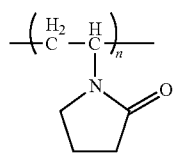

is water soluble, thereby the polymer containing oxazolinyl is water soluble, in other words, the polymer containing oxazolinyl can dissolve in water. The

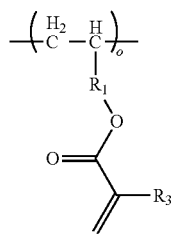

is ultraviolet (UV) curable, thereby the polymer containing oxazolinyl is UV curable. In other words, the polymer containing oxazolinyl can undergo a solidifying reaction when exposed to ultraviolet radiation. The polymer containing oxazolinyl is heat curable and UV curable, thus the water soluble photosensitive resin composition is heat curable and UV curable.

In at least one exemplary embodiment, the chemical structure formula of the polymer containing oxazolinyl is:

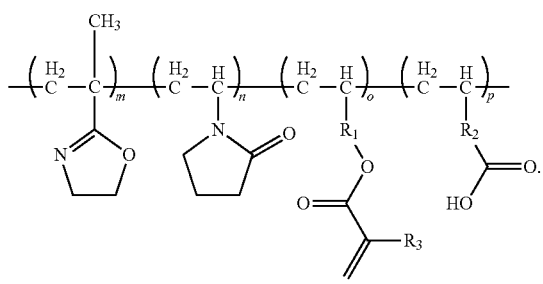

In the chemical structure formula of the polymer containing oxazolinyl above, the m, n, o, and p is each a positive integer. In at least one exemplary embodiment, the $R_1$ is $(CH_2)_k$, the k is a positive integer; the $R_2$ is $(CH_2)_t$, the t is a positive integer. The $R_3$ may be H or $CH_3$. The

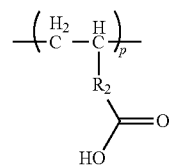

is also heat curable.

When temperature is higher than 150 degrees Celsius, the oxazolinyl and carboxyl (—COOH) can react with each other as follows:

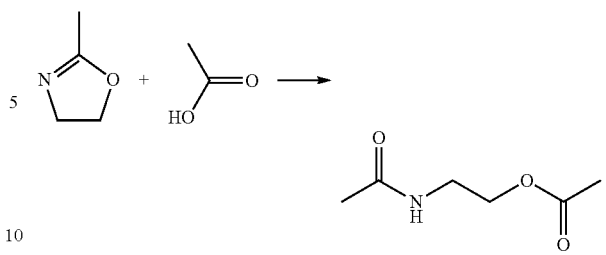

Thereby, when the polymer containing oxazolinyl is at a temperature higher than 150 degrees Celsius, the

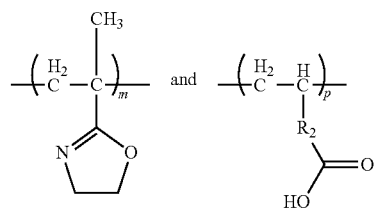

groups react with each other, in that longer chains are generated as the polymer containing oxazolinyl is polymerized. After the water soluble photosensitive resin composition is exposed to ultraviolet radiation and undergoes solidifying reaction to form a polymer, and the polymer is put under a temperature higher than 150 degrees Celsius, the polymer will continue to undergo thermal solidifying reaction, thereby an insulating layer that is formed by the water soluble photosensitive resin composition also has improved water resistance and chemical resistance.

The photosensitive monomer is configured to increase viscosity and adhesion strength of the water soluble photosensitive resin composition. The photosensitive monomer contains at least one ethoxy group. The photosensitive monomer can be polyethylene glycol dimethacrylate, ethoxylated 1,6-hexanediol diacrylate, 9,9-Bis[4-(2-acryloyloxyethyloxy)phenyl]fluorene, ethoxylated bisphenol A dimethacrylate, ethoxylated trimethylolpropane trimethacrylate, ethoxylated pentaerythritol tetraacrylate, ethoxylated dipentaerythritol hexaacrylate, or any combination thereof.

In at least one exemplary embodiment, the photosensitive monomer has a number of the ethoxy groups greater than or equal to 10, and the photosensitive monomer has a number of the carbon-carbon double bonds greater than or equal to 2. The photosensitive monomer thereby has a better UV curing property, and thereby an insulating layer formed by the water soluble photosensitive resin composition has improved water resistance and chemical resistance.

The photo-initiator can absorb ultraviolet radiation to generate free radicals or positive ions when the water soluble photosensitive resin composition is exposed to ultraviolet radiation. The free radicals or positive ions can cause the polymer containing oxazolinyl and photosensitive monomer to polymerize, to form a dense cross-linking network structure. The photo-initiator can be α-hydroxy ketones, acylphosphine oxide, amino ketone compound, oxime ester compound, or any combination thereof. In at least one exemplary embodiment, the photo-initiator can be 2-hydroxy-2-methyl-1-phenyl-1-acetone (photo-initiator-1173), 1-hydroxy cyclohexyl phenyl ketone (photo-initiator-184), Diphenyl(2,4,6-trimethylbenzoyl)phosphine oxide (photo-initiator-TOP), 2-methyl-4'-(methylthio)-2-morpholinopropiophenone (photo-initiator-907), phenyl bis(2,4,6-trimethylbenzoyl)-phosphine oxide (photo-initiator-819 or photo-initiator-819DW), 2-Benzyl-2-(dimethylamino)-4'-morpholinobutyrophenone (photo-initiator-369), 2,2-dimethoxy-2-phenylacetophenone, benzophenone (photo-initiator-BP), isopropyl thioxanthone (photo-initiator-ITX), carbazole oxime ester, or any combination thereof.

The water soluble photosensitive resin composition may further comprise a solvent. In at least one exemplary embodiment, the solvent is water.

The water soluble photosensitive resin composition may further comprise a coloring agent. The coloring agent is in an amount by weight of about 1 part to about 5 parts in the water soluble photosensitive resin composition.

The coloring agent can allow desired colors for the water soluble photosensitive resin composition. The coloring agent can be a pigment, a dye, or any combination thereof. The pigment can be an inorganic pigment, an organic pigment, or any combination thereof. The dye can be a natural organic dye, a synthesized organic dye, or any combination thereof.

The water soluble photosensitive resin composition may further comprise a filler. The filler is in an amount by weight of about 5 parts to about 30 parts in the water soluble photosensitive resin composition. The filler can be an inorganic filler, an organic filler, or any combination thereof. The inorganic filler may be barium sulfate ($BaSO_4$). The filler is configured to improve the mechanical properties of the photosensitive resin composition.

The water soluble photosensitive resin composition may further comprise an additive. The additive can be a thickening agent, a leveling agent, an antifoaming agent, a flame retardant, or any combination thereof.

The water soluble photosensitive resin composition does not comprise an organic solvent. The water soluble photosensitive resin composition is not only heat curable, but also ultraviolet curable. The water soluble photosensitive resin composition does not comprise an epoxy resin, thereby no reaction with the carboxyl groups contained in the water soluble photosensitive resin composition occurs. The polymer containing oxazolinyl cannot react with the carboxyl group contained in the water soluble photosensitive resin composition. Thereby the water soluble photosensitive resin composition may be stored at a normal atmospheric temperature over a long period.

FIG. 1 illustrates a flowchart of a method for making the water soluble photosensitive resin composition in accordance with an exemplary embodiment. The exemplary method is provided by way of example, as there are a variety of ways to carry out the method. Each block shown in the figure represents one or more processes, methods or subroutines, carried out in the exemplary method. Furthermore, the illustrated order of blocks is by example only, and the order of the blocks can change. Additional blocks may be added, or fewer blocks may be utilized, without departing from this disclosure. The exemplary method may begin at block 101.

At block 101, a polymer containing oxazolinyl, a photosensitive monomer, a photo-initiator, a coloring agent, and a solvent are mixed with a solvent to form a mixture. The polymer containing oxazolinyl is in an amount by weight of about 100 parts in the water soluble photosensitive resin composition, the photosensitive monomer is in an amount by weight of about 10 parts to about 50 parts in the water soluble photosensitive resin composition, and the photo-initiator is in an amount by weight of about 5 parts to about 15 parts in the water soluble photosensitive resin composition. The coloring agent is in an amount by weight of about 1 part to about 5 parts in the water soluble photosensitive resin composition. The amount of the solvent may be adjusted, ensuring that all the above components may be dissolved in the solvent.

At block 102, the mixture is stirred to cause the polymer containing oxazolinyl, the photosensitive monomer, the photo-initiator, and the coloring agent to be dispersed in the solvent, thereby forming a water soluble photosensitive resin composition.

Figure 2:
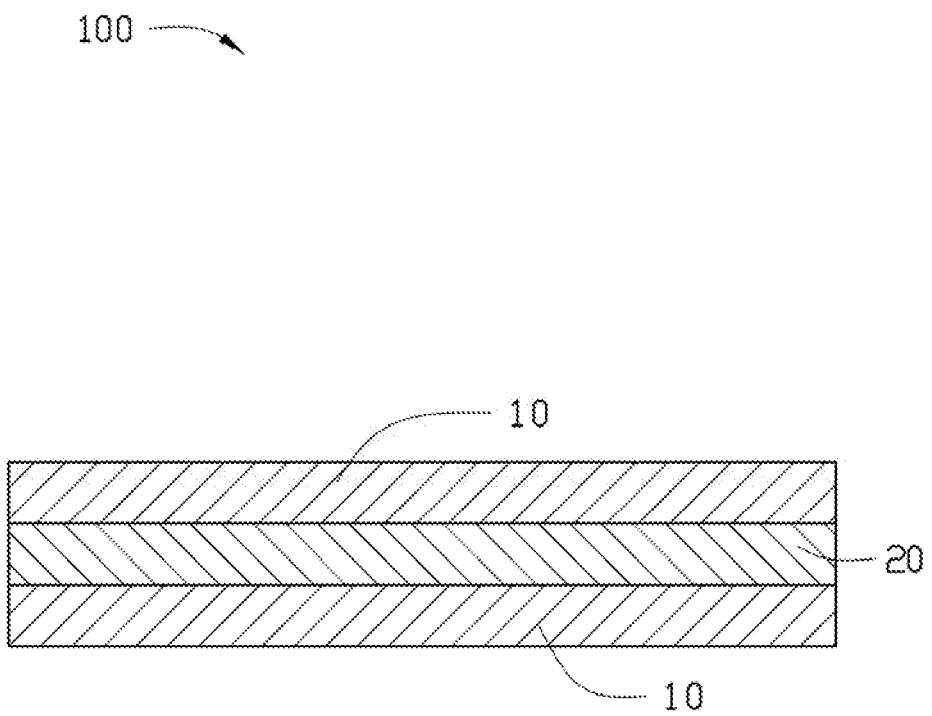
FIG. 2 is a diagram of an exemplary embodiment showing photosensitive resin composition being coated on a release film.

FIG. 2 illustrates an exemplary embodiment of a film 100 including a resin layer 20, and a release film 10 attached to at least one surface of the resin layer 20. The resin layer 20 is formed by coating the water soluble photosensitive resin composition on a surface of the release film 10 and then drying the water soluble photosensitive resin composition. The water soluble photosensitive resin composition can dissolve in water, thereby the resin layer 20 can also dissolve in water. The water soluble photosensitive resin composition is heat curable and UV curable, thereby the resin layer 20 is heat curable and UV curable too. The resin layer 20 includes an exposing area and a developing area. When the resin layer 20 undergoes an exposure and development process, the developing area is covered, but the exposing area is exposed to ultraviolet radiation to have the polymer containing oxazolinyl and photosensitive monomer undergo a solidifying reaction. Water is used as a developer to develop the developing area.

Figure 3:
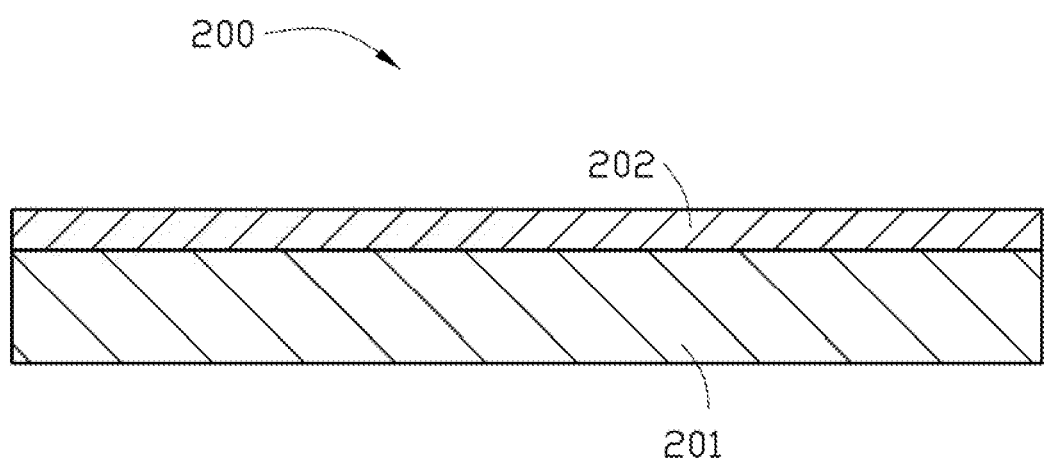
FIG. 3 is a diagram of a printed circuit board according to an exemplary embodiment of the present application.

FIG. 3 illustrates an exemplary embodiment of a printed circuit board 200 including a circuit substrate 201, and an insulating layer 202 attached to at least one surface of the circuit substrate 201. The insulating layer 202 is made by adhering the resin layer 20 to the surface of the circuit substrate 201 and applying exposure and development processes to the resin layer 20. When the polymer containing oxazolinyl in the resin layer 20 includes

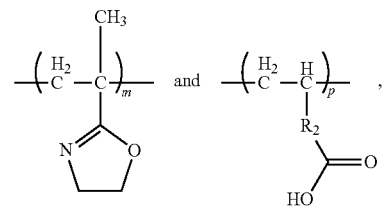

the resin layer 20 can be exposed to ultraviolet radiation to undergo ultraviolet solidifying reaction, and then heated to a temperature higher than 150 degrees Celsius to undergo thermal solidifying reaction. The ultraviolet solidifying reaction and heat solidifying reaction can form a cross-linking network structure, which can improve a cross-linking density of the photosensitive resin composition, so that the insulating layer 202 will have an improved quality of water resistance, chemical resistance, thermal resistance, flexibility, and adhesion strength.

Example 1

Polymer containing oxazolinyl, ethoxylated trimethylolpropane trimethacrylate, phenyl bis(2,4,6-trimethylbenzoyl)-phosphine oxide, coloring agent, water, and $BaSO_4$ were added into a container of 500 mL to form a mixture, the mixture was stirred to form a water soluble photosensitive resin composition.

The polymer containing oxazolinyl has a molecular weight of 20000 g/mol.

The mass of the polymer containing oxazolinyl is 100 g, the mass of the ethoxylated trimethylolpropane trimethacrylate is 40 g, and the mass of the phenyl bis(2,4,6-trimethylbenzoyl)-phosphine oxide is 8 g. The mass of the coloring agent is 2 g, the mass of the water is 100 g, and the mass of the $BaSO_4$ is 30 g.

Example 2

Polymer containing oxazolinyl, ethoxylated trimethylolpropane trimethacrylate, phenyl bis(2,4,6-trimethylbenzoyl)-phosphine oxide, coloring agent, water, and $BaSO_4$ were added into a container of 500 mL to form a mixture, and the mixture was stirred to form a water soluble photosensitive resin composition.

The polymer containing oxazolinyl has a molecular weight of 20000 g/mol.

The mass of the polymer containing oxazolinyl is 100 g, the mass of the ethoxylated trimethylolpropane trimethacrylate is 20 g, and the mass of the phenyl bis(2,4,6-trimethylbenzoyl)-phosphine oxide is 8 g. The mass of the coloring agent is 2 g, the mass of the water is 100 g, and the mass of the $BaSO_4$ is 15 g.

Comparative Example 1

Epoxy acrylate, trimethylolpropane propoxylate triacrylate, phenyl bis(2,4,6-trimethylbenzoyl)-phosphine oxide, coloring agent, methy ethyl ketone, and $BaSO_4$ were added into a container of 500 mL to form a mixture, the mixture was stirred to form a photosensitive resin composition.

The epoxy acrylate has a molecular weight of 10000 g/mol. The epoxy acrylate has an acidity value of 100 mgKOH/g.

The mass of the epoxy acrylate is 100 g, the mass of the trimethylolpropane propoxylate triacrylate is 20 g, and the mass of the phenyl bis(2,4,6-trimethylbenzoyl)-phosphine oxide is 8 g. The mass of the coloring agent is 2 g, the mass of the methy ethyl ketone is 30 g, and the mass of the $BaSO_4$ is 15 g.

Comparative Example 2

Epoxy acrylate, trimethylolpropane propoxylate triacrylate, phenyl bis(2,4,6-trimethylbenzoyl)-phosphine oxide, coloring agent, methy ethyl ketone, $BaSO_4$ and bisphenol A epoxy acrylate were added into a container of 500 mL to form a mixture, and the mixture was stirred to form a photosensitive resin composition.

The epoxy acrylate has a molecular weight of 10000 g/mol. The epoxy acrylate has an acidity value of 100 mgKOH/g. The bisphenol A epoxy acrylate has an epoxy equivalent of 188 g/eq.

The mass of the epoxy acrylate is 100 g, the mass of the trimethylolpropane propoxylate triacrylate is 20 g, and the mass of the phenyl bis(2,4,6-trimethylbenzoyl)-phosphine oxide is 8 g. The mass of the coloring agent is 2 g, the mass of the methy ethyl ketone is 30 g, and the mass of the $BaSO_4$ is 15 g. The mass of the bisphenol A epoxy acrylate is 18.5 g.

Resin layers were formed by the water soluble photosensitive resin compositions of the above examples 1-2 and the photosensitive resin compositions of the above comparative examples 1-2. The resin layers were performed by water development test. The test results are shown in table 1. The water development test was carried out by providing a circuit substrate including a copper layer, and coating each of the water soluble photosensitive resin compositions of the above examples 1-2 and the photosensitive resin compositions of the above comparative examples 1-2 on a surface of the copper layer. The water soluble photosensitive resin compositions of the above examples 1-2 and the photosensitive resin compositions of the above comparative examples 1-2 on the surface of the copper layer were baked at a temperature of about 80 degrees Celsius to about 110 degrees Celsius for 10 minutes to about 30 minutes. Resin layers were thus formed, each resin layer included an exposing area and a developing area. The developing area was covered and the exposing area was exposed to ultraviolet radiation having a power of about 150 $mJ/cm^2$ to about 500 $mJ/cm^2$. Water having a temperature of about 30 degrees Celsius to about 50 degrees Celsius was applied to the developing area for about 60 seconds to about 150 seconds. The circuit substrate having been developed was immersed in a copper chloride ($CuCl_2$) solution and any change in color of the developing area was observed. If the developing area changed color immediately, this showed that the developing area was developed and removed, and the resin layer can be developed by water. If no change in color in the developing area was observed, this shows that the developing area was not developed and removed, the resin layer could not be developed by water.

Printed circuit boards were formed by the water soluble photosensitive resin compositions of the above example 1-2 and the photosensitive resin compositions of the above comparative examples 1-2. The printed circuit boards were subjected to an adhesion strength test under ASTM standard, an alkali resistance test, a thermal resistance test, a flexibility test, and a storage stability test. The test results are shown in table 1. The alkali resistant test was carried out by immersing the printed circuit boards into a sodium hydroxide solution having a mass concentration of about 10% and observing whether the photosensitive solder masks were peeled off. The flexibility test was carried out by bending the printed circuit boards through 180 degrees Celsius and calculating the number of times until fracture. The thermal resistance test was carried out by exposing the printed circuit board to a temperature equal to or greater than 288 degrees Celsius for 30 seconds and observing whether the photosensitive solder masks were peeled off or dropped out from the printed circuit boards. The storage stability test under the normal temperature was carried out by storing the printed circuit boards made by the photosensitive resin compositions and the resin compositions for one month, and then repeating the adhesion strength test, the alkali resistance test, the thermal resistance test. Any deterioration in the test results was determined. If no deterioration occurred, the properties of the photosensitive resin compositions or the resin compositions remained unchanged during the storage, otherwise the properties were changed during the storage.

TABLE 1

| | product | | | |
| --- | --- | --- | --- | --- |
| property | example 1 | example 2 | comparative example 1 | comparative example 2 |
| water development | yes | yes | no | no |
| adhesion strength | 5 B | 5 B | 4 B | 4 B |
| alkali | not peeled | generate | dissolved | peeled off |

TABLE 1-continued

| property | product | | | |
| --- | --- | --- | --- | --- |
| | example 1 | example 2 | comparative example 1 | comparative example 2 |
| resistance | off after 30 minutes | minor holes after 30 minutes | | after 30 minutes |
| thermal resistance | 288 degrees Celsius for 30 seconds not peeled off | 288 degrees Celsius for 30 seconds not peeled off | 288 degrees Celsius for 30 seconds peeled off | 288 degrees Celsius for 30 seconds not peeled off |
| flexibility | 12 times unchanged | 8 times unchanged | 1 time unchanged | 1 time changed |
| storage stability | | | | |

Table 1 illustrates that resin layers formed by the water soluble photosensitive resin compositions of the above examples 1-2 can be developed by water, while the resin layers formed by photosensitive resin compositions of the above comparative examples 1-2 cannot be developed by water. Circuit boards formed by the water soluble photosensitive resin compositions of the above examples 1-2 have improved adhesion strength, alkali resistance, and flexibility, compared to circuit boards formed by photosensitive resin compositions of the above comparative examples 1-2. Circuit boards formed by the water soluble photosensitive resin compositions of the above examples 1-2 have improved thermal resistance, compared to circuit board formed by photosensitive resin compositions of the above comparative example 1. Circuit boards formed by the water soluble photosensitive resin compositions of the above examples 1-2 have improved storage stability, compared to circuit board formed by photosensitive resin compositions of the above comparative example 2.

The embodiments shown and described above are only examples. Even though numerous characteristics and advantages of the present technology have been set forth in the foregoing description, together with details of the structures and function of the present disclosure, the disclosure is illustrative only, and changes can be made in the detail, including in matters of shape, size, and arrangement of the parts within the principles of the present disclosure, up to and including, the full extent established by the broad general meaning of the terms used in the claims.

What is claimed is:

1. A water soluble photosensitive resin composition comprising:
   a polymer containing oxazolinyl;
   a photosensitive monomer; and
   a photo-initiator;
wherein each of the polymer containing oxazolinyl, the photosensitive monomer, and the photo-initiator is water soluble or water dispersible, both of the polymer containing oxazolinyl and the photosensitive monomer have a plurality of carbon-carbon double bonds, the photosensitive monomer comprises a plurality of ethoxy groups, the polymer containing oxazolinyl and the photosensitive monomer polymerize to form a dense cross-linking network structure when the water soluble photosensitive resin composition is exposed to ultraviolet radiation.

2. The water soluble photosensitive resin composition of claim 1, wherein the polymer containing oxazolinyl is in an amount by weight of about 100 parts in the water soluble photosensitive resin composition, the photosensitive monomer is in an amount by weight of about 10 parts to about 50 parts in the water soluble photosensitive resin composition, and the photo-initiator is in an amount by weight of about 5 parts to about 15 parts in the water soluble photosensitive resin composition.

3. The water soluble photosensitive resin composition of claim 1, wherein a chemical structure formula of the polymer containing oxazolinyl is:

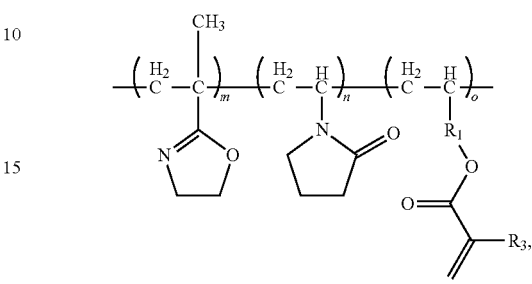

wherein each of the m, n, and o is a positive integer, the $R_1$ is $(CH_2)_k$, the k is a positive integer, and the $R_3$ is H or $CH_3$.

4. The water soluble photosensitive resin composition of claim 1, wherein a chemical structure formula of the polymer containing oxazolinyl is:

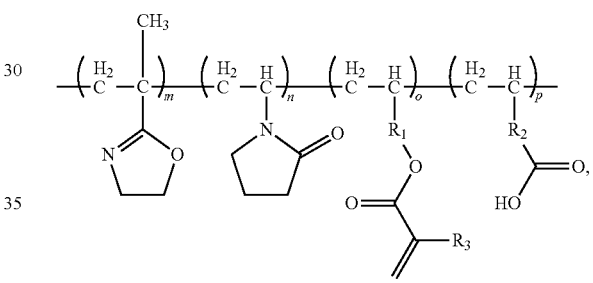

wherein each of the m, n, o, and p is a positive integer, the $R_1$ is $(CH_2)_k$, the k is a positive integer, the $R_2$ is $(CH_2)_t$, the t is a positive integer, and the $R_3$ is H or $CH_3$.

5. The water soluble photosensitive resin composition of claim 1, wherein a number of the ethoxy groups is greater than or equal to 10, a number of the carbon-carbon double bonds is greater than or equal to 2, the photosensitive monomer is selected from a group consisting of polyethylene glycol dimethacrylate, ethoxylated 1,6-hexanediol diacrylate, 9,9-Bis[4-(2-acryloyloxyethyloxy)phenyl]fluorene, ethoxylated bisphenol A dimethacrylate, ethoxylated trimethylolpropane trimethacrylate, ethoxylated pentaerythritol tetraacrylate, ethoxylated dipentaerythritol hexaacrylate, and any combination thereof.

6. The water soluble photosensitive resin composition of claim 1, wherein the photo-initiator is selected from a group consisting of α-hydroxy ketones, acylphosphine oxide, amino ketone compound, oxime ester compound, and any combination thereof, the photo-initiator is selected from a group consisting of 2-hydroxy-2-methyl-1-phenyl-1-acetone, 1-hydroxy cyclohexyl phenyl ketone, Diphenyl(2,4,6-trimethylbenzoyl)phosphine oxide, 2-methyl-4'-(methylthio)-2-morpholinopropiophenone, phenyl bis(2,4,6-trimethylbenzoyl)-phosphine oxide, 2-Benzyl-2-(dimethylamino)-4'-morpholinobutyrophenone, 2,2-dimethoxy-2-phenylacetophenone, benzophenone, isopropyl thioxanthone, and carbazole oxime ester, and any combination thereof.

7. The water soluble photosensitive resin composition of claim 1, wherein the water soluble photosensitive resin composition further comprise a solvent, the solvent is water.

8. The water soluble photosensitive resin composition of claim 1, wherein the water soluble photosensitive resin composition further comprise a coloring agent, the coloring agent is in an amount by weight of about 1 part to about 5 parts in the water soluble photosensitive resin composition.

9. The water soluble photosensitive resin composition of claim 1, wherein the water soluble photosensitive resin composition further comprise a filler, the filler is in an amount by weight of about 5 parts to about 30 parts in the water soluble photosensitive resin composition.

10. The water soluble photosensitive resin composition of claim 1, wherein the water soluble photosensitive resin composition further comprise an additive, the additive is selected from a group consisting of a thickening agent, a leveling agent, an antifoaming agent, a flame retardant, and any combination thereof.

11. A film comprising:
   at least one release film; and
   a resin layer, at least one surface of the resin layer is attached to a surface of the at least one release film, the resin layer is formed by a water soluble photosensitive resin composition, the water soluble photosensitive resin composition comprising:
   a polymer containing oxazolinyl;
   a photosensitive monomer; and
   a photo-initiator;
   wherein each of the polymer containing oxazolinyl, the photosensitive monomer, and the photo-initiator is water soluble or water dispersible, both of the polymer containing oxazolinyl and the photosensitive monomer have a plurality of carbon-carbon double bonds, the photosensitive monomer comprises a plurality of ethoxy groups, the polymer containing oxazolinyl and the photosensitive monomer polymerize to form a dense cross-linking network structure when the water soluble photosensitive resin composition is exposed to ultraviolet radiation.

12. The film of claim 11, wherein the polymer containing oxazolinyl is in an amount by weight of about 100 parts in the water soluble photosensitive resin composition, the photosensitive monomer is in an amount by weight of about 10 parts to about 50 parts in the water soluble photosensitive resin composition, and the photo-initiator is in an amount by weight of about 5 parts to about 15 parts in the water soluble photosensitive resin composition.

13. The film of claim 11, wherein a chemical structure formula of the polymer containing oxazolinyl is:

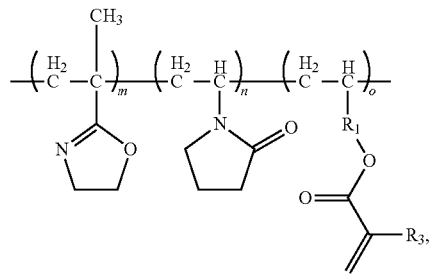

Wherein each of the m, n, and o is a positive integer, the $R_1$ is $(CH_2)_k$, the k is a positive integer, and the $R_3$ is H or $CH_3$.

14. The film of claim 11, wherein a chemical structure formula of the polymer containing oxazolinyl is:

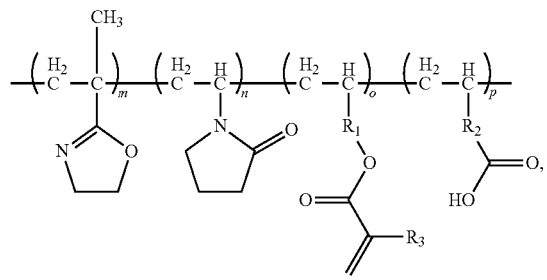

Wherein each of the m, n, o, and p is a positive integer, the $R_1$ is $(CH_2)_k$, the k is a positive integer, the $R_2$ is $(CH_2)_t$, the t is a positive integer, and the $R_3$ is H or $CH_3$.

15. The film of claim 11, wherein a number of the ethoxy groups is greater than or equal to 10, a number of the carbon-carbon double bonds is greater than or equal to 2, the photosensitive monomer is selected from a group consisting of polyethylene glycol dimethacrylate, ethoxylated 1,6-hexanediol diacrylate, 9,9-Bis[4-(2-acryloyloxyethyloxy)phenyl]fluorene, ethoxylated bisphenol A dimethacrylate, ethoxylated trimethylolpropane trimethacrylate, ethoxylated pentaerythritol tetraacrylate, ethoxylated dipentaerythritol hexaacrylate, and any combination thereof.

16. The film of claim 11, wherein the photo-initiator is selected from a group consisting of α-hydroxy ketones, acylphosphine oxide, amino ketone compound, oxime ester compound, and any combination thereof, the photo-initiator is selected from a group consisting of 2-hydroxy-2-methyl-1-phenyl-1-acetone, 1-hydroxy cyclohexyl phenyl ketone, Diphenyl(2,4,6-trimethylbenzoyl)phosphine oxide, 2-methyl-4'-(methylthio)-2-morpholinopropiophenone, phenyl bis(2,4,6-trimethylbenzoyl)-phosphine oxide, 2-Benzyl-2-(dimethylamino)-4'-morpholinobutyrophenone, 2,2-dimethoxy-2-phenylacetophenone, benzophenone, isopropyl thioxanthone, and carbazole oxime ester, and any combination thereof.

17. The film of claim 11, wherein the water soluble photosensitive resin composition further comprise a solvent, the solvent is water.

18. The film of claim 11, wherein the water soluble photosensitive resin composition further comprise a coloring agent, the coloring agent is in an amount by weight of about 1 part to about 5 parts in the water soluble photosensitive resin composition.

19. The film of claim 11, wherein the water soluble photosensitive resin composition further comprise a filler, the filler is in an amount by weight of about 5 parts to about 30 parts in the water soluble photosensitive resin composition.

20. The film of claim 11, wherein the water soluble photosensitive resin composition further comprise an additive, the additive is selected from a group consisting of a thickening agent, a leveling agent, an antifoaming agent, a flame retardant, and any combination thereof.

* * * * *